Figure 1:
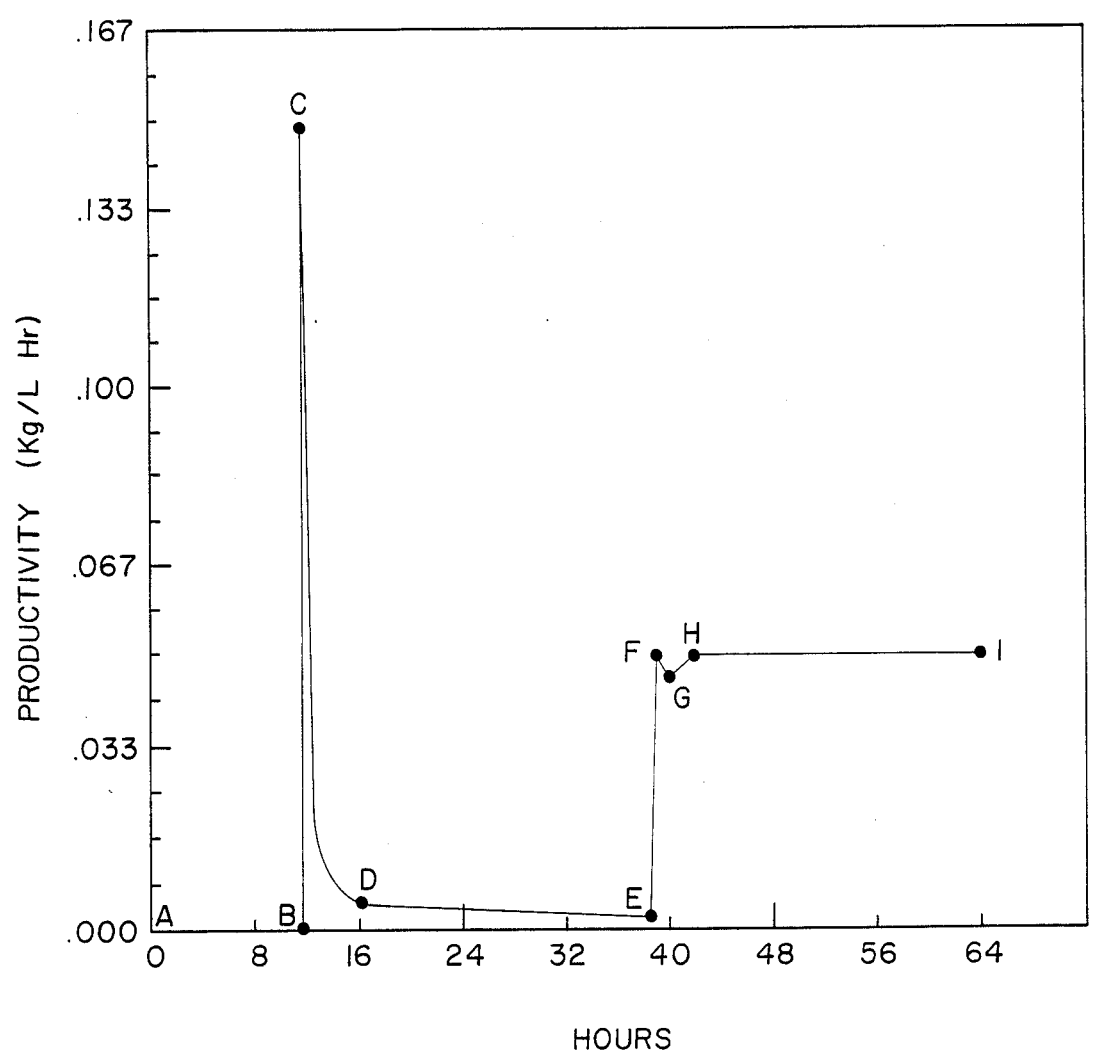

United States Patent [19]

Holbrook et al.

[11] Patent Number: 4,962,247
[45] Date of Patent: Oct. 9, 1990

[54] PROCESS FOR THE PRODUCTION OF HALOGENATED HYDROCARBONS

[75] Inventors: Michael T. Holbrook, Baton Rouge, La.; Timothy Juhlke, Round Rock, Tex.

[73] Assignee: The Dow Chemical Company, Midland, Mich.

[21] Appl. No.: 295,864

[22] Filed: Jan. 10, 1989

[51] Int. Cl.$^5$ .................. C07C 17/00; C07C 19/02
[52] U.S. Cl. ................................ 570/240; 570/150
[58] Field of Search ............................. 570/150, 240

[56] References Cited

U.S. PATENT DOCUMENTS 4,041,087  8/1977  Vannice ........................ 570/240
4,538,011  8/1985  Drago et al. .................... 570/240

Primary Examiner—J. E. Evans
Attorney, Agent, or Firm—James M. Pelton; Paul D. Hayhurst; Richard G. Waterman

[57] ABSTRACT

This invention relates to a process for continuously producing halogenated hydrocarbons by: (1) flowing a feed mixture containing CO, H2 and a halogen source into a reaction zone containing a catalyst bed; (2) removing from the reaction zone the resultant reaction product which contains the desired halogenated hydrocarbons; and (3) maintaining the halogen source content in the feed mixture at from about the stoichiometric amount to about twice the stoichiometric amount needed to produce the halogenated hydrocarbons.

18 Claims, 1 Drawing Sheet

PROCESS FOR THE PRODUCTION OF HALOGENATED HYDROCARBONS

CROSS REFERENCE TO RELATED APPLICATION

This application is a Continuation-in-part of Application Ser. No. 063,932, filed June 19, 1987, now abandoned.

BACKGROUND OF THE INVENTION

This invention relates to a catalytic process for producing halogenated hydrocarbons from a halogen, and a hydrogen and carbon monoxide containing gas, e.g., synthesis gas.

The halogenation of a variety of hydrocarbon feedstocks produces many valuable and useful products. Typical of such halogenated hydrocarbons is methyl chloride which is used in the production of higher halogenated hydrocarbons, silicones and tetramethyllead.

There are two principal processes for producing methyl chloride, i.e., the chlorination of methane and the reaction of hydrogen chloride and methanol. Both of these processes require the use of an intermediate, methane for the former and methanol, typically obtained by reforming methane, for the latter. These intermediates add expense to the selected process whether they are purchased from a supplier or produced for in-plant use.

In recent years, there has been an increase in the number of synthesis gas plants being built. These plants produce synthesis gas by the gasification of carbonaceous materials, especially coal. During the 1970's, the high price of oil made such plants economically attractive; however, due to present lower oil prices, such plants provide an excess of synthesis gas capacity. It would be desirable, then, to be able to use this excess capacity to directly produce methyl chloride and other halogenated hydrocarbons from synthesis gas.

Therefore, it is an object of this invention to provide a process for the direct production of halogenated hydrocarbons using hydrogen- and carbon monoxide-containing gases, especially synthesis gas.

THE INVENTION

This invention relates to a process for continuously producing halogenated hydrocarbons of the formula $C_nH_{2n+2-z}X_z$ by: (1) flowing a feed mixture containing $H_2$, CO and a halogen source into a reaction zone containing a catalytic bed: (2) removing from the reaction zone the resultant reaction product which contains the desired halogenated hydrocarbons: and (3) maintaining the halogen source content in the feed mixture at from about the stoichiometric amount to about twice the stoichiometric amount needed to produce the halogenated hydrocarbons.

The $C_nH_{2n+2-z}X_z$ halogenated hydrocarbon products of the subject process are those defined by the following identities for n, z and X: n is a whole positive integer which is $\geq 4$; z is a whole positive integer which is $\geq 10$ and X is a halogen radical, i.e., F—, Cl—, Br—, or I—. Also, $2n+2-z$ must have a whole integer value which is $>0$. The most predominate product produced by the process is methyl halide. However, other halogenated methanes, ethanes, propanes and butanes may be co-produced. Exemplary of such co-products are methylene halide, methylhaloform, carbon tetrahalide, haloethane, dihaloethane, trihalopropane, and dihalobutane. The halogen substituent of the halogenated hydrocarbon is preferably chlorine as chlorinated products find a ready and extensive market.

The CO and $H_2$ constituents of the feed mixture are conveniently provided by synthesis gas, however, synthesis gas need not be the sole source for such constituents. Instead, the $H_2$ and CO constituents can be provided from separate and independent sources. The halogen source can be either molecular halogen or hydrogen halide. For example, when X is Cl—, the halogen source can be $Cl_2$ or HCl.

The molar ratio between $H_2$ and CO in the feed mixture is within the range of from about 1:1 to about 20:1 and is preferably within the range from about 2:1 to about 12:1. Molar ratios below 1:1 are not desirable as the reaction will be hydrogen deficient. Molar ratios above 12:1 are not as desirable as others in the above given broad range as too much hydrogen promotes hydrogenation of the halogenated hydrocarbon products resulting in a loss of process efficiency. The optimum molar ratio is one which balances the competing needs of providing sufficient $H_2$ to the reaction without unduly promoting the hydrogenation reaction.

In the initial stage of the subject process, the flow of halogen source to the reaction zone is steadily increased and a concomitant increase in the production rate of halogenated hydrocarbon product is observed until a maximum rate is achieved. A decrease in product production rate is then noted if the flow of the halogen source is increased further. This decrease is probably due to a decrease in the catalytic activity of the catalytic bed brought about by an excessively high concentration of halogen source in the reaction zone. After noting the decrease, the halogen source flow to the reaction zone is adjusted to achieve the steady state stage for the subject process by obtaining a halogen source content in the feed mixture which is between near stoichiometric and twice stoichiometric, relative to the halogenated hydrocarbons produced. Within this range, the amount of halogen source can be maintained to achieve the production rate desired. A preferred production rate is preferably the maximum production rate obtained in the initial stage. Generally, the mole ratio of $H_2$:CO:X at the steady state stage is kept within the range of 1–20:1:0.01–0.10 and preferably within the range of 2–12:1:0.03–0.09. A most highly preferred range is within the range of 2–12:1:0.03–0.07.

The catalytic bed material is comprised of an acidic inorganic oxide material and a catalyst material selected from the group consisting of a Group VIII metal, Re or mixtures thereof. Typically, the Group VIII metals are Fe, Co, Ni, Ru, Rh, Pd, Os, Ir and Pt. Thus, combinations of these or of these with Re are useful. The catalyst is either mixed with the acidic inorganic oxide or is, preferably, supported in a dispersed state on the acidic inorganic oxide. Alumina, silica-alumina, zeolite, etc., are exemplary of conventional acidic inorganic oxide materials which may be used. Of these, alumina is preferred.

A unique acidic inorganic oxide material is an aluminum-phosphorus material in which the atom ratio of aluminum to phosphorus is within the range of from about 50:1 to about 2:1 and preferably within the range from about 20:1 to about 6:1. This material is prepared by first forming an aluminum alkoxide/alkoxy-substituted phosphate gel. The aluminum-phosphorus material is then obtained from the gel by subjecting the gel to a heat treatment which burns therefrom substantially all of the gel's non-oxygen and non-metal constituents.

The gel is formed by dissolving the aluminum alkoxide in a solvent, such as nitric acid, and adding to the resultant solution the alkoxy-substituted phosphate. The alkoxy constituents of the aluminum hydroxide and the alkoxy phosphate may contain up to 8 carbon atoms and are exemplified by ethoxy and isopropoxy radicals. The obtained mix is heated and stirred until a gel forms. The gel is heated initially to a temperature of from about 100° C. to about 120° C. for several hours, say 12 hours, to convert it to a solid form. The solid is then sintered at a first elevated temperature, e.g., 250° C. to 300° C., and then at a second elevated temperature, e.g., 400° C. to 600° C. Higher temperatures may be used, i.e., temperatures up to 900° C., to achieve, at the expense of surface area, a structurally stronger material. Temperatures above 900° C. should be avoided as the pore structure of the material begins to collapse and there is a rapid loss of surface area.

The aluminum-phosphorus material has been found to give better catalytic activity to the catalytic bed over a wider temperature range as compared against the use of alumina. Generally, the maximum activity for alumina is observed to occur at a process temperature within the range of 250° C. to 300° C., depending upon the type of alumina and reaction conditions used. At higher temperatures, the activity decreases. The aluminum phosphorus material, instead, shows a steady increase in catalytic activity to temperatures beyond 325° C.

Preferred catalysts are platinum, palladium, iridium, rhodium, or mixtures thereof. Palladium is preferred due to its methyl halide selectivity and high activity. When the inorganic acid oxide material is alumina, the catalyst in the catalytic bed is present in an amount within the range of from about 0.1 wt. % to about 10 wt. % based upon the total weight of the catalytic bed. With a palladium/alumina combination, a preferred range for the palladium content is from about 1 wt. % to about 5 wt. %. When the oxide material is the aluminum-phosphorus material, the catalyst is present in an amount within the range of from about 0.1 wt. % to about 10 wt %. With palladium and the aluminum-phosphorus material, a preferred range for the palladium content is from about 1 wt. % to about 5 wt.%.

The catalyst may be incorporated into the catalytic bed by most conventional methods, one method typically includes impregnation of the acidic inorganic oxide material, which is in the support form, with a halide salt of the catalyst. Drying and calcining methods are then performed, all as is well known in the art. For the process of this invention, conventional reduction of the catalyst may or may not be performed. The halide salt of the catalyst is preferably chosen so that the halide identity of the salt is the same as the halogen substituent of the halogenated hydrocarbon products sought.

To enhance the catalytic activity of the catalytic bed, alkali and alkali earth metal promoters, especially lithium or sodium, may be added thereto. Other promoters, such as molybdenum and lanthanum, may also be suitable. The lithium promoter may be present in the catalytic bed in an amount within the range of from about 0.1 wt. % to about 0.6 wt. % while the sodium may be present in an amount within the range of from about 0.3 wt. % to about 0.8 wt. %. The foregoing weight percentages are based upon the total weight of the catalytic bed. These promoters can be incorporated into the catalytic bed by well known procedures. For example, the acidic organic oxide material, in support form, can be impregnated with an aqueous halide, nitrate or carbonate salt of the metal and then conventionally dried and calcined. Reduction may or may not be performed. The preferred salt is the halide salt which is of the same halide as the halogen constituent of the halogenated hydrocarbon products sought. These promoters are effective in causing an increase in the production rate and selectivity of the halogenated hydrocarbon products.

The use of the foregoing promoters is preferably accompanied with, at the steady state stage, the use of an amount of halogen source in the feed mixture which is in excess of stoichiometric as regards the halogenated hydrocarbon products produced. This excess is required to maximize the production rate of the halogenated products. Generally speaking, an excess up to about 100% of the stoichiometric amount is preferred.

The residence time in the reaction zone for the reaction gases, which gases contain feed mixture constituents, reaction intermediates and halogenated hydrocarbon products, should be within the range of from about 1 second to about 20 seconds and preferably within the range of from about 2 seconds to about 10 seconds. Residence times greater than 20 seconds are detrimental to production rates as the halogenated hydrocarbon products will, in significant amounts, begin to be absorbed onto the catalytic bed and be hydrogenated to yield a less halogenated hydrocarbon product and a halo-acid. In the continuous process of this invention, residence time in seconds equals 3600 divided by space velocity. Space velocity is the number of catalyst volumes of gas which pass over the catalytic bed in one hour under reaction zone conditions.

The temperature within the reaction zone is within the range of from about 180° C. to about 400° C. and preferably within the range of from about 230° C. to about 330° C. For the higher temperatures, i.e., temperatures over 300° C., the before discussed aluminum-phosphorus material is preferably used. Generally, a pressure range of from about 10 atmospheres to about 300 atmospheres is suitable. A preferred pressure range is from about 30 atmospheres to about 100 atmospheres.

Various features of the process of this invention are exemplified by the accompanying drawing in which:

FIG. 1 is a plot of $CH_3Cl$ production versus time.

The plot shown in FIG. 1 depicts a $CH_3Cl$ production history for a process of this invention starting from the initial charging of the reactor with the catalytic bed and ending at achievement of the steady state stage for the $CH_3Cl$ production rate. Starting at zero time and at point A, the catalytic bed is placed into the reactor. The period of time between point A and point B is utilized in conditioning the catalytic bed for initiation of process operation. At point B, $H_2$ and CO are introduced into the reactor and brought into reactive contact with the catalytic bed. As can be seen from the plot, the production rate of $CH_3Cl$ increases quickly to point C and then decreases over a short period of time to point D. This very quick rise in $CH_3Cl$ production rate between points B and C is due to the utilization of the chlorine found on the catalytic bed, which chlorine is a residue from the particular production technique used in preparing the catalytic bed. The rather precipitous drop in $CH_3Cl$ production rate from point C to point D shows that the available chlorine on the catalytic bed has been nearly depleted. If the catalytic bed is not produced by a technique which results in a chlorine residue, then the production of CH$_3$Cl during the time period between A and F does not occur.

At the initiation of the process of this invention, H$_2$, CO and a chloride source are fed to the reaction zone at point E. The flow of chloride source to the reaction zone is increased relative to the flow of the other reactant gases until the CH$_3$Cl production rate goes through a maximum at point F and begins to decrease at point G. The chloride source relative flow to the reaction zone is then decreased until the production rate is again at the maximum, point H. This rate can then be maintained as shown at Point I.

During the initial increase in activity (from point E to point F) the CH$_3$Cl forming reaction is limited by the small amount of chloride present in the feed gases. Very high chloride conversions are obtained in this area. As the chloride source flow is increased further relative to the other feed gas flows the chloride acts as a poison and begins to interfere with CH$_3$Cl production. This effect of chloride is well known in the literature. Thus the productivity decreases from point F to point G. Excess chloride tolerance is dependent on the catalyst makeup. This chloride buildup is reversible such that when the chloride source flow is decreased relative to the other feed gas flows the excess chloride is removed from the catalyst allowing the productivity to increase back to point H.

Chloride conversion in the area of the curve from point E to point F and from point H to point I is from about 50% to nearly 100%. Thus, the proper amount of chloride to be in the feed stream ranges from about that stoichiometrically required to produce the product to about twice that amount giving the observed chloride conversions. This amount must be experimentally determined for the particular catalyst used.

The following Examples are illustrative of various features of the process of this invention and are not to be taken as limiting the scope of the invention.

EXAMPLES

In the following Examples, various (1) catalytic bed materials, (2) reaction temperatures and pressures, (3) H$_2$ to CO molar ratios and (4) space velocities were used in combination with one another to illustrate various processes of this invention at steady state.

To form the catalytic bed, a Group VIII metal catalyst was conventionally impregnated, in a dispersed state, on the indicated inorganic oxide material. Such impregnation was affected by dissolving a chloride salt of the Group VIII metal and using the incipient wetness technique to achieve the impregnation. In those Examples where an alkali metal promoter was used, the promoter was impregnated on the inorganic oxide material by the same process.

The aluminum-phosphate material used in some of the Examples was formed in the following manner. To a 500 cc erylenmeyer flask was added 0.2 M of aluminum isopropoxide and 300 cc of water. These contents were heated to about 90° C. and stirred. Then, 3 cc of concentrated HNO$_3$ were added. The resultant mix was heated for about 1 hour until nearly all of the solid dissolved. The flask was then heated and stirred until the resultant solution became translucent with a bluish color which was indicative of the formation of colloidal or polymeric species. When the viscosity of the solution began to increase, 0.2 M triethoxy phosphate was added in one portion. (The viscosity was somewhat less than glycerine.) The triethoxy phosphate caused the viscosity to drop to a watery consistency. The flask contents were heated and water was added as needed to maintain the same general volume. The heat and stirring was continued until the solutions once again thickened and eventually solidified into a gel.

The gel was then placed in an oven for about 15 hours at 100°–110° C. After this heating, the gel was converted to a solid with the solid being about ⅛–1/10 of the gel's previous volume. The solid was then sintered at higher temperatures. It was first heated to 275° C. and allowed to stand for an hour, then heated to 400° C. and allowed to stand for an hour. This treatment caused the carbon-containing compounds to be burned out cleanly. The solid was then heated to 550° C. for 3 hours.

The reactor used was a ¼" (0.635 cm) stainless steel tube. The catalytic bed material was not reduced prior to being placed in the reactor. At process initiation, a 4:1 molar ratio mixture of H$_2$ and CO was passed over the catalyst at 250° C. and 33 atmospheres. A sharp increase in the production rate of CH$_3$Cl was noted followed by a sharp decrease in such production. Subsequent to the noted decrease in the CH$_3$Cl production, a 20% by volume HCl in He stream was introduced into the tube reactor. The H$_2$ and CO were added as a 120 ml/min stream while the HCl was added as a 50 ml/min stream. This mixture was passed through the catalytic bed at 275° C. and 33 atm. until the production of CH$_3$Cl was noted. The HCl stream was maintained until a decrease in the CH$_3$Cl production rate was seen. After the CH$_3$Cl production rate fell, the HCl flow was adjusted, in those Examples where no promoter was used, to achieve stoichiometric equality (Examples 1–25 and 60–62) with the CH$_3$Cl being produced. For those Examples where a promoter was used, Examples 26–59, the HCl provided in the feed mixture was up to 100% in excess of stoichiometric or whatever excess was necessary to maximize halogenated hydrocarbon production. Since the other halogenated hydrocarbons being produced by the reaction were not substantial, the stoichiometric relationships between HCl and CH$_3$Cl closely approximates the stoichiometric relationship between HCl and all the halogenated hydrocarbons produced by the process. After 2 hours from the time of adjustment, the productivity of CH$_3$Cl had stabilized and the process was deemed to be at steady state.

TABLE I

| Ex. No. | Catalyst | Temp. (°C.) | Pressure atm. | Molar Ratio H$_2$/CO | Space Velocity @STP (hr$^{-1}$) | Space Velocity under Reaction Conditons (hr$^{-1}$) | Productivity kgCH$_3$Cl/l hr |
|---|---|---|---|---|---|---|---|
| 1 | 0.5% Pt/Al$_2$O$_3$[1] | 300 | 13 | 2:1 | 12 | 1.9 | 0.0006 |
| 2 | 1.75 Pt/Al$_2$O$_3$ | 300 | 33 | 4:1 | 255 | 15 | 0.0011 |
| 3 | 0.5% Ir/Al$_2$O$_3$[1] | 350 | 33 | 4:1 | 250 | 16 | |
| 4 | 0.9 Pd/Al$_2$O$_3$ | 300 | 14 | 4:1 | 256 | 37 | 0.0008 |

TABLE I-continued

| Ex. No. | Catalyst | Temp. (°C.) | Pressure atm. | Molar Ratio H$_2$/CO | Space Velocity @STP (hr$^{-1}$) | Space Velocity under Reaction Conditons (hr$^{-1}$) | Productivity kgCH$_3$Cl/1 hr |
|---|---|---|---|---|---|---|---|
| 5 | 4.8% Pd/Al$_2$O$_3$ | 250 | 33 | 4:1 | 261 | 14 | 0.0018 |
| 6 | 2% Pd/SiO$_2$ | 250 | 33 | 4:1 | 261 | 14 | 0.0014 |
| 7 | 1% Pd/ZrO$_2$ | 250 | 33 | 4:1 | 261 | 14 | 0.0016 |
| 8 | 5% Pd/ZrO$_2$ | 250 | 33 | 4:1 | 782 | 42 | 0.0047 |
| 9 | 5% Pd/MgO | 250 | 33 | 4:1 | 856 | 46 | |
| 10 | 5% Pd/Al$_2$O$_3$[3] | 300 | 33 | 4:1 | 781 | 46 | 0.0074 |
| 11 | 5% Pd/Al$_2$O$_3$[4] | 250 | 33 | 4:1 | 782 | 42 | 0.0091 |
| 12 | 5% Pd/Al$_2$O$_3$[5] | 250 | 33 | 4:1 | 782 | 42 | 0.0083 |
| 13 | 5% Pd/Al$_2$O$_3$ | 275 | 33 | 4:1 | 746 | 42 | 0.0120 |
| 14 | 5% Pd/Al$_2$O$_3$ | 275 | 33 | 4:1 | 1,865 | 105 | 0.0199 |
| 15 | 5% Pd/Al$_2$O$_3$ | 275 | 67 | 4:1 | 2,928 | 82 | 0.0327 |
| 16 | 5% Pd/Al$_2$O$_3$[5] | 275 | 33 | 12:1 | 3,569 | 203 | 0.0252 |
| 17 | 5% Pd/Al$_2$O$_3$[5] | 275 | 33 | 12:1 | 18,005 | 1,024 | 0.0876 |
| 18 | 5% Pd/Al$_2$O$_3$[5] | 300 | 33 | 12:1 | 14,394 | 856 | 0.1053 |
| 19 | 5% Pd/Al$_2$O$_3$[5] | 300 | 33 | 12:1 | 17,993 | 1,070 | 0.1194 |
| 20 | 5% Pd/Al$_2$O$_3$[5] | 250 | 31 | 12:1 | 7,199 | 4.12 | 0.0350 |

1 - Catalyst marketed by Engelhardt Industries, Div., Englehardt Minerals & Chemicals Corporation.
2 - Catalyst marketed by Calsicat Division of Mallinckrodt, Inc.
3 - Al$_2$O$_3$ material marketed under the designation Al-4133 by Harshaw/Filtrol Partnership.
4 - Al$_2$O$_3$ material marketed under the designation SA6275 by Norton Company.
5 - Al$_2$O$_3$ material marketed under the designation 89372 by Alfa Product.
All other Al$_2$O$_3$ material marketed under the name Catapal SB by Conoco, Inc.

TABLE II

| Ex. No. hr | Catalyst | Temp. (°C.) | Pressure atm. | Molar Ratio H$_2$/CO | Space Velocity @STP (hr$^{-1}$) | Space Velocity under Reaction Conditions (hr$^{-1}$) | Productivity kgCH$_3$Cl/1 hr |
|---|---|---|---|---|---|---|---|
| 21 | 5% Pd/Al$_2$O$_3$ | 276 | 33 | 4:1 | 15,725 | 896 | 0.0674 |
| 22 | 5% Pd/Al$_2$O$_3$ | 276 | 33 | 4:1 | 5,897 | 336 | 0.0353 |
| 23 | 5% Pd/Al$_2$O$_3$ | 301 | 33 | 4:1 | 15,891 | 945 | 0.0835 |
| 24 | 5% Pd/Al$_2$O$_3$ | 325 | 33 | 4:1 | 16,161 | 1,003 | 0.1107 |
| 25 | 5% Pd/Al$_2$O$_3$ | 325 | 33 | 4:1 | 6,074 | 377 | 0.0449 |
| 26 | 5% Pd/Al$_2$O$_3$ + 0.2% Li | 275 | 33 | 4:1 | 15,860 | 902 | 0.0835 |
| 27 | 5% Pd/Al$_2$O$_3$ + 0.2% Li | 275 | 33 | 4:1 | 6,048 | 344 | 0.0514 |
| 28 | 5% Pd/Al$_2$O$_3$ + 0.2% Li | 275 | 33 | 4:1 | 5,925 | 337 | 0.0385 |
| 29 | 5% Pd/Al$_2$O$_3$ + 0.2% Li | 300 | 33 | 4:1 | 15,924 | 947 | 0.0867 |
| 30 | 5% Pd/Al$_2$O$_3$ + 0.2% Li | 325 | 33 | 4:1 | 16,032 | 995 | 0.1172 |
| 31 | 5% Pd/Al$_2$O$_3$ + 0.2% Li | 325 | 33 | 4:1 | 6,123 | 380 | 0.0562 |
| 33 | 5% Pd/Al$_2$O$_3$ + 0.5% Li | 275 | 33 | 4:1 | 5,996 | 341 | 0.0449 |
| 34 | 5% Pd/Al$_2$O$_3$ + 0.5% Li | 300 | 33 | 4:1 | 15,924 | 947 | 0.1011 |
| 32 | 5% Pd/Al$_2$O$_3$ + 0.5% Li | 275 | 33 | 4:1 | 15,737 | 895 | 0.0738 |
| 35 | 5% Pd/Al$_2$O$_3$ + 0.5% Li | 325 | 33 | 4:1 | 16,241 | 1,008 | 0.1316 |
| 36 | 5% Pd/Al$_2$O$_3$ + 0.5% Li | 325 | 33 | 4:1 | 6,139 | 381 | 0.0578 |
| 37 | 5% Pd/Al$_2$O$_3$ + 1.0% Li | 275 | 33 | 4:1 | 6,646 | 378 | 0.0209 |
| 38 | 5% Pd/Al$_2$O$_3$ + 1.0% Li | 275 | 33 | 4:1 | 17,301 | 984 | 0.0353 |
| 39 | 5% Pd/Al$_2$O$_3$ + 1.0% Li | 300 | 33 | 4:1 | 17,640 | 1,049 | 0.0433 |
| 40 | 5% Pd/Al$_2$O$_3$ + 1.0% Li | 325 | 33 | 4:1 | 17,837 | 1,107 | 0.0626 |
| 41 | 5% Pd/Al$_2$O$_3$ + 1.58% Li | 275 | 33 | 4:1 | 5,961 | 339 | 0.0016 |
| 42 | 5% Pd/Al$_2$O$_3$ + 1.58% Li | 275 | 33 | 4:1 | 15,209 | 865 | 0.0225 |
| 43 | 5% Pd/Al$_2$O$_3$ + 0.2% Na | 275 | 33 | 4:1 | 5,785 | 329 | 0.0305 |
| 44 | 5% Pd/Al$_2$O$_3$ + 0.2% Na | 275 | 33 | 4:1 | 15,367 | 874 | 0.0465 |
| 45 | 5% Pd/Al$_2$O$_3$ + 0.2% Na | 300 | 33 | 4:1 | 15,655 | 931 | 0.0658 |
| 46 | 5% Pd/Al$_2$O$_3$ + 0.2% Na | 325 | 33 | 4:1 | 15,871 | 985 | 0.0835 |
| 47 | 5% Pd/Al$_2$O$_3$ + 0.2% Na | 325 | 33 | 4:1 | 5,962 | 370 | 0.0337 |
| 48 | 5% Pd/Al$_2$O$_3$ + 0.2% Na | 275 | 33 | 4:1 | 5,785 | 329 | 0.0273 |
| 49 | 5% Pd/Al$_2$O$_3$ + 0.50% Na | 275 | 33 | 4:1 | 6,013 | 342 | 0.0465 |
| 50 | 5% Pd/Al$_2$O$_3$ + 0.50% Na | 275 | 33 | 4:1 | 15,701 | 893 | 0.0690 |
| 51 | 5% Pd/Al$_2$O$_3$ + 0.50% Na | 300 | 33 | 4:1 | 16,008 | 952 | 0.1075 |
| 52 | 5% Pd/Al$_2$O$_3$ + 0.50% Na | 325 | 33 | 4:1 | 16,209 | 1,006 | 0.1156 |
| 53 | 5% Pd/Al$_2$O$_3$ + 0.50% Na | 325 | 33 | 4:1 | 6,074 | 377 | 0.0385 |
| 54 | 5% Pd/Al$_2$O$_3$ + 0.22% Cs | 277 | 33 | 4:1 | 5,606 | 320 | 0.0144 |
| 55 | 5% Pd/Al$_2$O$_3$ + 0.22% Cs | 277 | 33 | 4:1 | 14,768 | 843 | 0.0257 |
| 56 | 5% Pd/Al$_2$O$_3$ + 0.22% Cs | 300 | 33 | 4:1 | 14,949 | 889 | 0.0417 |
| 57 | 5% Pd/Al$_2$O$_3$ + 0.22% Cs | 300 | 33 | 4:1 | 15,134 | 900 | 0.0305 |
| 58 | 5% Pd/Al$_2$O$_3$ + 0.22% Cs | 325 | 33 | 4:1 | 15,307 | 950 | 0.0498 |
| 59 | 5% Pd/Al$_2$O$_3$ + 0.22% Cs | 325 | 33 | 4:1 | 16,096 | 999 | 0.0161 |

TABLE III

| Ex. No. | Catalyst | Temp. (°C.) | Pressure atm. | Molar Ratio H₂/CO | Space Velocity @STP (hr⁻¹) | Space Velocity under Reaction Conditons (hr⁻¹) | Productivity kgCH₃Cl/1 hr |
|---|---|---|---|---|---|---|---|
| 60 | Pd/Al—P* | 275 | 33 | 4:1 | 17,811 | 1,013 | 0.0517 |
| 61 | Pd/Al—P* | 300 | 33 | 4:1 | 17,825 | 1,060 | 0.0865 |
| 62 | Pd/Al—P* | 325 | 33 | 4:1 | 17,820 | 1,106 | 0.1246 |

*Al—P = Aluminum-phosphorus material with an Al:P atom ratio of 8:1.

As shown in the Tables above the production of methyl chloride is carried out without difficulty and with more efficiency than previous batch processes. Illustrative data from the above examples are presented in Table IV below to show the CO conversion and the residence time. Residence time is an important indication of efficiency.

TABLE IV
RESULTS OF CO CONVERSION AND RESIDENCE TIME CALCULATIONS FOR SELECTED EXAMPLES

| Example No. | CO Conversion (%) | Residence Time (sec.) |
|---|---|---|
| 13 | 3.8 | 4.8 |
| 16 | 4.0 | 1.0 |
| 18 | 4.2 | 0.3 |
| 21 | 1.0 | 0.2 |
| 22 | 1.4 | 0.6 |
| 23 | 1.2 | 0.2 |
| 24 | 1.6 | 0.2 |
| 25 | 1.7 | 0.6 |
| 30 | 1.7 | 0.2 |
| 31 | 2.1 | 0.6 |
| 35 | 1.8 | 0.2 |
| 36 | 2.2 | 0.6 |
| 40 | 0.8 | 0.2 |
| 41 | 0.5 | 0.6 |
| 46 | 1.2 | 0.2 |
| 52 | 1.6 | 0.2 |
| 58 | 1.1 | 0.2 |

What is claimed is:

1. A process for preparing halogenated hydrocarbons of the formula $C_nH_{2n+2-z}X_z$ wherein n is a whole positive integer less than or equal to four, z is a whole positive integer less than or equal to ten, $2n+2-z$ is a whole integer less than or equal to zero, and X is a halogen radical, which process comprises:
   (a) maintaining a reaction zone at a temperature within the range of from about 180° C. to about 400° C. and at a pressure within the range of from about 10 atmospheres to about 300 atmospheres, said reaction zone containing a catalytic bed comprising an acidic inorganic oxide material and a catalyst selected from the group consisting of a Pt, Pd, Ir, Rh metal and mixtures thereof;
   (b) continuously flowing a feed mixture comprising CO, H₂ and, as a halogen source, molecular halogen or hydrogen halide into said zone and into reactive contact with said catalytic bed;
   (c) continuously removing from said reaction zone a resultant reaction product, which product contains said halogenated hydrocarbons, the removal being effected so as to provide a reaction time within the range of from about 1 second to about 20 seconds; and
   (d) maintaining the amount of said halogen source in said feed mixture so that the molar ratio of H₂:CO:halogen source is within the range of 1-20:1:0.01-0.10.

2. The process of claim 1 wherein said acidic inorganic oxide is alumina.

3. The process of claim 1 wherein said acidic inorganic oxide is an aluminum-phosphorus support material having an atom ratio of aluminum to phosphorus within the range of from about 50:1 to about 2:1.

4. The process of claim 1 wherein said catalyst is a non-reduced catalyst.

5. The process of claim 1 wherein said catalyst is a reduced catalyst.

6. The process of claim 1 wherein said catalyst is palladium.

7. The process of claim 6 wherein said acidic inorganic oxide is alumina.

8. The process of claim 6 wherein said palladium comprises from about 0.1 wt. % to about 10 wt. % of said catalytic bed.

9. The process of claim 1 wherein said catalytic bed additionally contains a lithium or a sodium promoter, and wherein the amount of said halogen source in said feed mixture is maintained so that the molar ratio of H₂:CO:halogen source is within the range of 2-12:1:0.03-0.09.

10. The process of claim 9 wherein said lithium promoter comprises from about 0.1 wt. % to about 0.6 wt. % of said catalytic bed and said sodium promoter comprises from about 0.3 wt. % to about 0.8 wt. % of said catalytic bed.

11. The process of claim 10 wherein said catalyst is palladium and wherein said palladium comprises from about 0.1 wt. % to about 10 wt. % of said catalytic bed.

12. The process of claim 11 wherein said acidic inorganic oxide is alumina.

13. The process of claim 3 wherein the atom ratio of said aluminum to said phosphorus is within the range of from about 50:1 to about 2:1.

14. The process of claim 13 wherein said catalyst is palladium and said palladium comprises from about 0.1 wt. % to about 10 wt. % of the catalytic bed.

15. The process of claim 13 wherein said catalytic bed additionally contains a lithium or a sodium promoter, and wherein the amount of said halogen source in said feed mixture is maintained so that the molar ratio of H₂:CO:halogen source is within the range of 2-12:1:0.03-0.09.

16. The process of claim 15, wherein said lithium promoter comprises from about 0.1 wt. % to about 0.6 wt. %.of said catalytic bed and said sodium promoter comprises from about 0.3 wt. % to about 0.8 wt. % of said catalytic bed.

17. The process of claim 14 wherein said catalytic bed additionally contains a lithium or a sodium promoter, and wherein the amount of said halogen source in said feed mixture is maintained so that the molar ratio of H$_2$:CO:halogen source is within the range of 2–12:1:0.0.03–0.07.

18. The process of claim 18 wherein said lithium promoter comprises from about 0.1 wt. % to about 0.6 wt. % of said catalytic bed and said sodium promoter comprises from about 0.3 wt. % to about 0.8 wt. % of said catalytic bed.

* * * * *